United States Patent
Preston et al.

(10) Patent No.: US 6,814,719 B2
(45) Date of Patent: Nov. 9, 2004

(54) FEMALE URINARY SYSTEM

(75) Inventors: Theresa M. Preston, Bear, DE (US); Ivars V. Ivansons, Wilmington, DE (US); Dudley Spencer, Wilmington, DE (US)

(73) Assignee: Denco, Inc., Wilmington, DE (US)

( * ) Notice: Subject to any disclaimer, the term of this patent is extended or adjusted under 35 U.S.C. 154(b) by 92 days.

(21) Appl. No.: 10/366,124

(22) Filed: Feb. 13, 2003

(65) Prior Publication Data

US 2004/0162535 A1 Aug. 19, 2004

(51) Int. Cl.⁷ .................................................. A61F 5/44
(52) U.S. Cl. ...................................... 604/329; 600/574
(58) Field of Search .............................. 604/329, 331, 604/332, 330, 327; 600/573, 574

(56) References Cited

U.S. PATENT DOCUMENTS 4,889,532 A * 12/1989 Metz et al. ................. 604/330
5,053,027 A * 10/1991 Manfredi .................... 604/329
6,592,560 B2 * 7/2003 Snyder ....................... 604/331

* cited by examiner

Primary Examiner—Kevin T. Truong

(57) ABSTRACT

A female urinary system comprises an appliance including a hollow open top urine receiving body having a peripheral rim for fitting under the urethra. The body includes a receiving portion which would be located below the urethra and which merges into a discharge bowl having a discharge opening leading to an integral downwardly extending discharge tube. The discharge tube preferably has a spiral groove in its outer surface to permit the tube to bend without kinking or otherwise cutting off flow through the tube. The appliance also includes a vent located at the highest portion of the appliance. The vent includes a vent hole extending completely through the wall of the appliance and a vent groove leading from the hole to the spiral groove. The central axis of the urine receiving body is at an obtuse angle with respect to the longitudinal axis of the discharge tube.

24 Claims, 3 Drawing Sheets

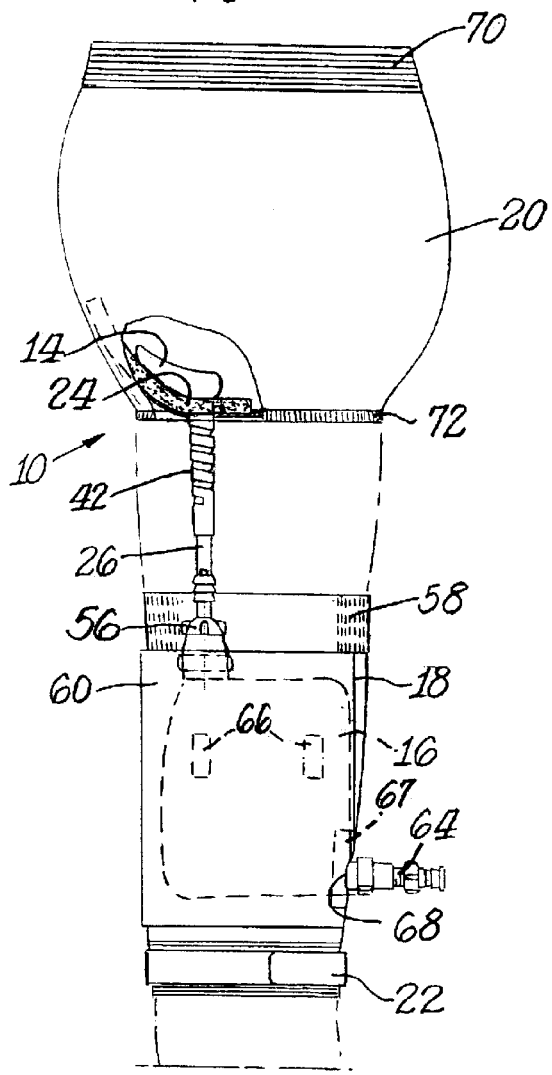
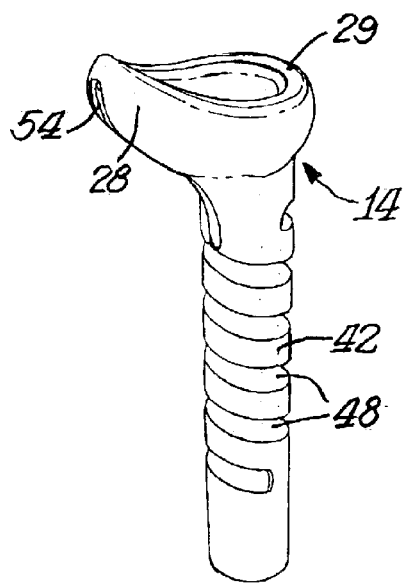
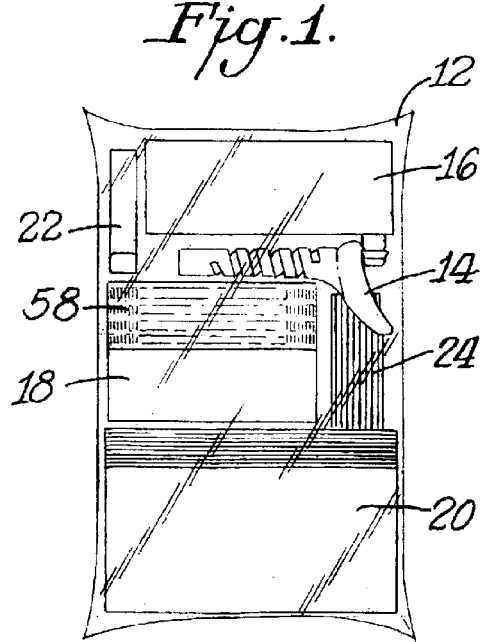

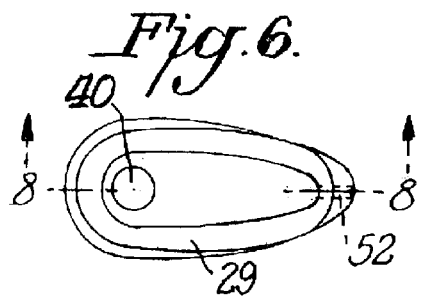
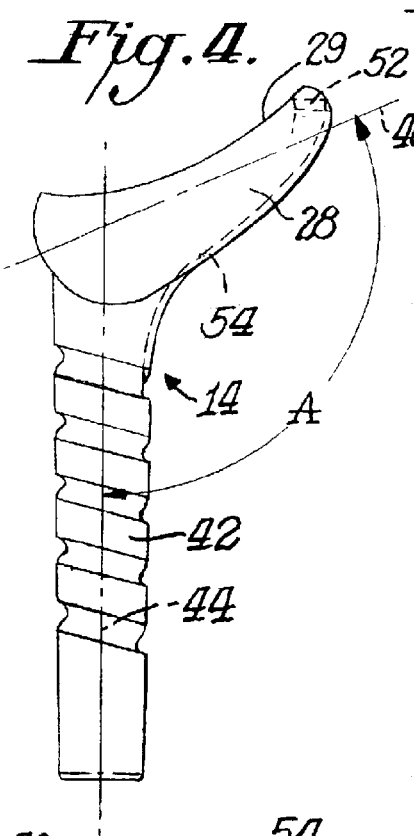
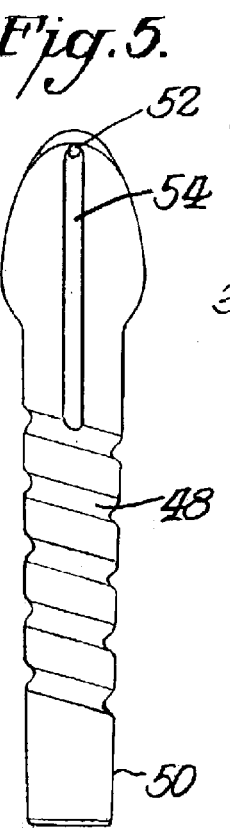
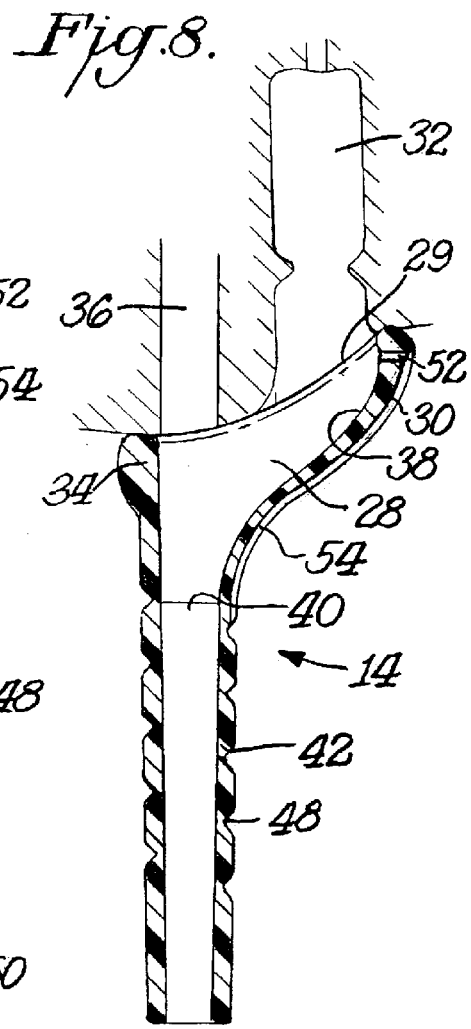
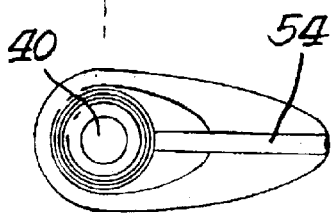
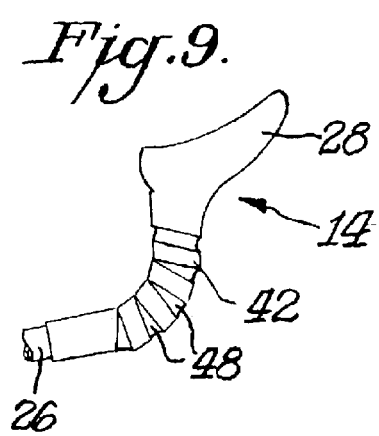

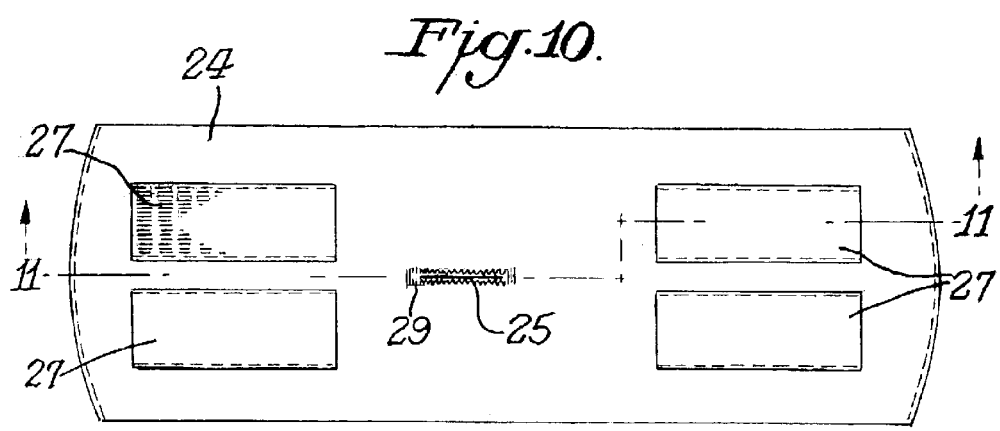
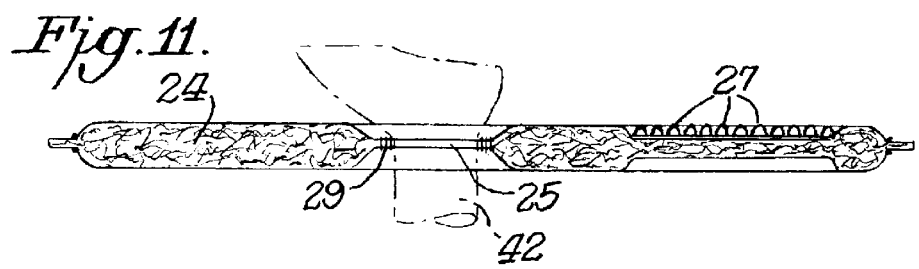

FEMALE URINARY SYSTEM

BACKGROUND OF THE INVENTION

For decades urinary incontinence or incontinency has been associated with shame, embarrassment and silence even though the World Health Organization estimates that there are 200 million worldwide with symptoms of male or female urinary incontinence. A true number is not known because the problem is so under reported. It is estimated that urinary incontinence affects 25 million Americans. This condition impacts quality of life by interfacing with work, travel, social recreation and is associated with an increased number of falls, urinary tract infections arid skin breakdown. Professionals are only recently learning progressive therapies for incontinence and many lay persons are still keeping their problem a secret. Prevention of this problem is a relatively new concept with little research data reported. Factors involved in bladder and/or sphincter problems and pelvic support are being looked at for preventing some forms of urinary incontinence.

SUMMARY OF THE INVENTION

A female urinary system includes an appliance having a hollow open top urine receiving body with a peripheral rim for fitting under the urethra so that urine may flow into the body. The body has a receiving portion which would be located below the urethra. The receiving portion merges into a discharge bowl. A discharge opening or passage is located in the discharge bowl which communicates with a downwardly extending discharge tube. The central axis of the body forms an angle greater than 90° with respect to the longitudinal axis of the discharge tube. The discharge tube includes bending structure on its outer surface to permit the discharge tube to bend without kinking and without cutting off flow of urine through the discharge tube. An important feature of the invention is a vent located in the receiving portion of the body generally at the peripheral rim.

In a preferred practice of the invention the bending structure of the discharge tube is a spiral groove in its outer surface. The vent includes a hole extending in generally the uppermost part of the receiving portion of the body slightly below the peripheral rim. The vent further includes a vent groove which leads from the vent hole and extends to the spiral groove.

The angle between the central axis of the body and the longitudinal axis of the discharge tube is preferably in the range of 110°–140° and most preferably is 120°.

The appliance is preferably part of a kit which also includes a collection bag which in use would be in flow communication with the discharge tube. The kit further includes a leg sleeve which would be worn on the leg of the user. The leg sleeve preferably includes a pocket into which the collection bag would be inserted. The kit further preferably includes panties where the appliance would be located and an absorbent pad which would be mounted in the panties below the receiving body of the appliance.

THE DRAWINGS

FIG. 1 is a top plan view of a kit for the female urinary system of this invention;

FIG. 2 is a side elevational view showing the female urinary system of this invention mounted in use;

FIG. 3 is a perspective view of the appliance member of the system of FIG. 1;

FIG. 4 is a side elevational view of the appliance shown in FIG. 3;

FIG. 5 is a front elevational view of the appliance shown in FIGS. 3–4;

FIGS. 6 and 7 are top and bottom plan views of the appliance shown in FIGS. 3–5;

FIG. 8 is a cross-sectional view taken through FIG. 6 along the line 8-8;

FIG. 9 is a side elevational view of the appliance shown in FIGS. 3–6 in a bent condition;

FIG. 10 is a top plan of an absorbent pad usable in the system of this invention; and FIG. 11 is a cross sectional view taken through FIG. 10 along the line 10-10.

DETAILED DESCRIPTION

FIGS. 1–2 illustrate the various components or members of the female urinary system 10 in accordance with this invention. As shown in FIG. 1 the components are stored in a package or kit 12. FIG. 2 shows the various components when mounted on a user. Referring again to FIG. 1 the container 12 is preferably a sealed pouch which may be made of any suitable plastic material heat sealed to a closed condition after the components of system 10 have been placed in the container. If desired, container 12 may be made from a transparent material. As illustrated in FIG. 1 the components include an appliance 14, a collection bag 16, a leg sleeve 18, panties 20, sets of belts 22 and one or more absorbent pads 24. Each of these components may be individually packaged in its own sealed bag. Any other components of the system 10, such as connector tube 26 shown in FIG. 2 would also be packaged in container 12, such as by being in its own separate sealed bag. Most of the components of system 10 could be reusable. Other components, such as pad 24 would be a consumable pad. Accordingly, the package or kit may include a plurality of such pads; or the pads could be purchased separately as needed.

FIGS. 3–9 show the details of appliance 14. As shown therein appliance 14 includes a hollow open top urine receiving body 28 having a receiving portion 30 which would be located below the urethra 32 as shown in FIG. 8. Receiving portion 30 merges into a discharge bowl 34 located below the vagina 36. Urine receiving body 28 includes a peripheral rim 29 for fitting under the urethra 32 and vagina 36.

Body 28 has a tapered inner wall 38 which tapers downwardly toward discharge opening or passage 40. Downwardly extending discharge tube 42 is preferably integrally formed with body 28 to comprise a portion of appliance 14. Thus, the urine may flow from the urethra 32 into body 28 and then through discharge tube 42.

An important feature of this invention is the orientation of body 28 with respect to discharge tube 42. As shown in FIG. 4 discharge tube 42 includes a longitudinal axis 44, while body 28 has a central axis 46. The angle A formed between axis 44 and axis 46 is a diverging angle, namely, one which is greater than 90°. The preferred angle is in the range of 110°–140° while the most preferred is 120°, or about 120° such as from 117° to 123°. This diverging angle permits drainage from appliance 14 from all positions of the user. In addition, the shape of appliance 14 is such that it seals in back of the vagina 36. As illustrated, body 28 is of generally egg-shape as best shown in FIG. 6. As illustrated therein the egg-shape is generally elliptical but has its laterally widest portion closer to the bowl portion of body 28. Discharge opening 40 is located at this laterally widest portion of the egg shape at the central axis. As also shown in, for example, FIGS. 4 and 8 the upper peripheral rim 29 is dished out as viewed in its side profile.

Discharge tube 42 includes bending structure to facilitate the bending of discharge tube 42 without resulting in any kinking or cutting off of flow through discharge tube 42. Any suitable form of bending structure could be used, such as forming the outer surface in accordion shape or having hinged portions. Preferably the bending structure is a spiral or helical groove 48 which is formed in the outer surface of discharge tube 42. The upper end of spiral groove 48 is located at about the location of discharge opening 40. The spiral groove terminates a short distance above its lower end. This provides a smooth uninterrupted lower end portion 50 which could have a connector tube 26 mounted on the outer surface of discharge tube 42. Preferably, as shown in FIG. 2, connector tube 26 is telescopically inserted inside the hollow passage of discharge tube 42.

As shown in FIG. 9 if discharge tube 42 is caused to bend because of movement of the user, the tube can assume the bent condition without kinking or otherwise preventing flow of urine through the discharge tube.

Another important feature of the invention is the provision of vent structure to create a vacuum break. As a result there is rapid and free flow of the urine through appliance 14. The vent structure includes a vent hole 52 which is at the generally highest portion of appliance 14. As best illustrated in FIG. 8 vent hole 52 is located at and slightly below the peripheral rim 29 in the urine receiving portion 30 of body 28. Vent hole 52 extends completely through the wall of body 28 to communicate with the hollow interior. Vent hole 52 also communicates with a longitudinal groove 54 extending in the outer surface of body 28 until it connects with spiral groove 48. Thus, the spiral groove in combination with the vent groove and vent hole assure proper venting of appliance 14.

In use as shown in FIG. 2 panties 20 would be worn by the user. Panties 20 includes a slit or slot so that appliance 14 could be located inside panties 20 with the discharge tube 42 extending through the slit. As also illustrated in FIG. 2 an absorbent pad 24 similar to a conventional sanitary napkin would also be placed in panties 20 below body portion 28. As shown in FIGS. 10–11, pad 24 would include a slit 25, preferably located along the longitudinal centerline of the pad body but at least slightly off center with respect to the transverse center line of the pad body. The slit could extend partially across the transverse center, as illustrated, or could be completely spaced from the transverse center line aligned with the slit in panties 20 to permit drain tube 42 to extend through the pad 24 as well as through the panties 20. Pad 24 and/or panties 20 could include securing structure 27, such as Velcro® or any other securing structure, on the lower surface of the pad body. FIG. 10 illustrates the fastening structure 27 at four symmetrically spaced locations, preferably at least partially longitudinally outwardly of the slit 25. Because slit 25 is longitudinally offset a longer portion of pad 24 extends away from tube 42 than the other portion as shown in FIG. 2 to properly orient and mount the pad and panties together. The slit 25 of pad 24 is preferably reinforced, such as by peripheral stitching 29. Panties 20 could also be reinforced in the general area of the pad 24 and appliance 14.

As shown in FIG. 2 a collection bag 16 is located below discharge tube 42. Collection bag 16 could include a valve 56, such as a read valve, at its upper end to control the flow of urine into bag 16 without permitting the urine to flow back into discharge tube 42 depending on the physical position of the user. If desired, discharge tube 42 may be mounted directly to valve 56. As illustrated, however, a connection tube 26 creates the flow communication between bag 16 and discharge tube 42.

In accordance with a further feature of this invention the kit includes a leg sleeve 18. Leg sleeve 18 has an open top and an open bottom. An integral elastic band 58 may be at the top and/or bottom of sleeve 18 to firmly mount the sleeve on the thigh of the user. If desired, a separate strap or belt 22 could be mounted around the top and/or bottom of the sleeve 18. Such belt could be adjustably mounted through the use of suitable fasteners such as Velcro® hook and loop formations. Sleeve 18 includes a pouch or pocket 60 into which the bag 16 would be placed. As a result, the bag is not only mounted properly in place, but also the bag is not located directly against the skin. As shown in FIG. 2 bag 16 includes a drain tube 64 which may have an outlet valve to permit periodic draining of the urine. Any suitable outlet valve may be used such as a screw or rotational valve which would be opened when desired.

Bag 16 is preferably generally rectangularly shaped. Although, for the sake of illustration, FIG. 2 illustrates the top and bottom edges of bag 16 to be shorter than the side edges, in the preferred practice of the invention the top and bottom are the longer edges which would thereby permit the bag 16 to wrap to a greater degree around the leg thereby increasing the capacity of the bag 16.

If desired, loops or guide tunnels 66 could be included on the outer surface of bag 16. These loops or guide tunnels 66 could be used for mounting the bag when the bag is disassembled from the remainder of the system such as during cleaning.

Pocket 60 may be formed by having longitudinal side edges permanently secured, by stitching or otherwise, to the main portion of sleeve 18. The top edge of pocket 60 could be left permanently open or could be selectively closed through the use of various fasteners such as Velcro® fasteners. Similarly the bottom edge of pocket 16 could be permanently secured to sleeve 18 or detachably secured. The ability to have the top and bottom selectively open facilitates the insertion and removal of collection bag 16 from sleeve 18. Slit 68 would be selectively closable by any suitable fastening structure 67 such as Velcro®.

While there may be concern with conventional female incontinence devices that the flow of urine could move into the vagina it has been found that the appliance 14 does not have such result.

Appliance 14 could be made of any suitable material such as medical grade silastic. Appliance 14 should have sufficient flexibility to permit bending particularly bending of the discharge tube 42 as well as to permit conforming to the female anatomy.

If desired, panties 20 could also be held in place by a harness strapped to the waistband 70. Waistband 70 as well as leg band 72 are preferably made of elastic material to firmly hold the panties in place. The construction of the panties is such that it could also be used to accommodate a catheter as well as the appliance 14.

In use, periodically or when a sufficient amount of urine has been collected in collection bag 16, the bag 16 can be completely replaced by closing the drain valve 56 to prevent further flow into bag 16 and from discharge tube 42. Bag 16 could then be removed and a new bag attached whereupon the drain valve 56 could again be opened. The invention could be practiced where the drain valve 56 is left mounted to the collector tube 26 and is not part of the collection bag 16. Thus, the closed drain valve would remain connected to collector tube 26 thereby assuring no further flow out of collector tube 26 during the process of changing bags. Alternatively, the bag 16 could be emptied by opening the valve in drain tube 64 at the bottom of bag 16.

As shown in FIG. 2 the inlet of collection bag 16 where valve 56 is located is obliquely opposite the location of the drain tube 64. By having the drain tube 64 and inlet at obliquely opposite corners there is further assurance of maximizing the capacity of collection bag 16.

By selection of the materials of construction and of the price of a kit incorporating the components of the system 10, it is possible to have different models available, such as models that could be usable for 10 hours or 100 hours or 1,000 hours. The short time use would be for a system that is disposable after a single use. Such use could be non-postoperative. The device for intermediate time use could be disposable after use, but could be used in postoperative hospital conditions. The long term version could be for chronic use and could be reusable. Such use for acute and chronic incontinence and for postoperative urinary drainage eliminates the danger of urinary tract infection. The system 10 is discreet, unobtrusive and comfortable. When used with a sanitary napkin 24 the sanitary napkin could function for menses and/or other discharges. The appliance 14 does not interfere with menstrual periods or with anal discharges while the appliance is mounted in place thereby avoiding accidental urinary tract contaminants. The system 10 can be used intermittently for activities such as social, travel or continuous use with urinary tract infection therapy or chronic incontinence. Thus, the system 10 could be used for short periods of time or as a semi-permanent device that can be used for extended periods of time (months) with the ability to be removed and replaced easily for sanitary cleaning purposes (daily). Since urine is a sterile fluid, the system is regularly flushed thus avoiding sepsis when in use. The collection receptacle, such as bag 16 can have its contents drained at will by an aseptic hand operated urine exit valve in tube 64. The system 10 provides an extremely comfortable device when in use and is effective from upright, sitting or supine positions.

What is claimed is:

1. A female urinary system comprising an appliance, said appliance including a hollow open top urine receiving body, said body having a receiving portion for being located below the urethra whereby urine may flow from the urethra into said receiving portion, said receiving portion merging into a discharge bowl, said body having a peripheral rim for fitting under the urethra, a discharge opening in said discharge bowl, a downwardly extending discharge tube connected to said discharge bowl and communicating with said discharge opening, said body having a central axis, said discharge tube having a longitudinal axis, said central axis and said longitudinal axis forming an angle greater than 90° when said appliance is in its inactive condition, said discharge tube having bending structure on its outer surface to permit said discharge tube to bend without kinking and without cutting off flow of urine through said discharge tube, and a vent in said receiving portion generally at said peripheral rim.

2. The system of claim 1 wherein said bending structure is a spiral groove in said outer surface of said discharge tube.

3. The system of claim 2 wherein said vent includes a hole in generally the uppermost part of said receiving portion slightly below said peripheral rim.

4. The system of claim 3 wherein said vent further includes a vent groove on the outer surface of said receiving portion, and said vent groove communicating with said hole and said spiral groove.

5. The system of claim 4 wherein said angle between said central axis and said longitudinal axis is in the range of 110°–140°.

6. The system of claim 5 wherein said angle is about 120°.

7. The system of claim 5 wherein receiving body is of egg shape, and said peripheral rim having a dished out side profile.

8. The system of claim 7 wherein said discharge opening is located at said central axis in the laterally widest portion of said egg shape, and said discharge tube being integral with said body.

9. The system of claim 8 including a collection bag, and said discharge tube communicating with said collection bag.

10. The system of claim 9 wherein said collection bag includes a drain tube.

11. The system of claim 10 including a leg sleeve for fitting around the leg of the user, said leg sleeve having a pocket with an open top, said collection bag being in said pocket, said pocket having a slit near its bottom, and said drain tube extending through said slit.

12. The system of claim 11 including panties, an absorbent pad in said panties, said appliance being in said panties with said discharge tube extending through said panties, a hole through said absorbent pad, said discharge tube extending through said pad hole, and said receiving body being above and in contact with said pad.

13. The system of claim 12 wherein said leg bag is of generally rectangular shape which is longer transversely than it is longitudinally, said leg bag drain tube being located at the bottom of said leg bag, and said drain tube being valve operated.

14. The system of claim 13 including a connector tube, said collection bag having an inlet in generally one of its upper corners, said connector tube being in flow communication with said inlet, a flow control valve at said inlet, and said drain tube being located generally at a bottom corner of said collection bag obliquely opposite said inlet.

15. The system of claim 3 including a collection bag, and said discharge tube communicating with said collection bag.

16. The system of claim 15 including a leg sleeve for fitting around the leg of the user, said leg sleeve having a pocket with an open top, said collection bag being in said pocket, said pocket having a slit near its bottom, and said drain tube extending through said slit.

17. The system of claim 1 wherein said angle between said central axis and said longitudinal axis is in the range of 110°–140°.

18. The system of claim 17 wherein said angle is about 120°.

19. The system of claim 1 including a collection bag, and said discharge tube communicating with said collection bag.

20. The system of claim 19 including a leg sleeve for fitting around the leg of the user, said leg sleeve having a pocket with an open top, said collection bag being in said pocket, said pocket having a slit near its bottom, and a drain tube extending through said slit.

21. The system of claim 1 including an absorbent pad, said pad having a slit extending completely therethrough, and said discharge tube extending through said slit.

22. The system of claim 21 wherein said slit is longitudinally centrally located in said pad, said slit being reinforced, said slit being transversely offset, and fastening structure at spaced locations on an outer surface of said pad.

23. The system of claim 1 in the form of a kit, said kit including a sealed container, said appliance being in said container, a collection bag in said container, a leg sleeve in said container, panties in said container, and an absorbent pad in said container.

24. The system of claim 21 wherein each of said appliance and said collection bag and said leg sleeve and said panties and said absorbent pad is in its own sealed bag in said sealed container.

* * * * *